United States Patent [19]

Proksch et al.

[11] 4,216,117
[45] Aug. 5, 1980

[54] LIPOPROTEIN DILUENT OR SOLUTION AND METHOD USEFUL IN THE PREPARATION OF ASSAY REFERENCE MATERIALS

[76] Inventors: Gary J. Proksch, 5514 N. Greenview Dr., Indianapolis, Ind. 46220; Dean P. Bonderman, 586 W. 77th South Dr., Indianapolis, Ind. 46260

[21] Appl. No.: 905,967

[22] Filed: May 15, 1978

[51] Int. Cl.$^2$ .................. G01N 31/00; G01N 33/16
[52] U.S. Cl. ............................... 252/408; 23/230 B
[58] Field of Search ....................... 23/230 B; 252/408

[56] References Cited

U.S. PATENT DOCUMENTS

| | | | |
|---|---|---|---|
| 3,260,648 | 7/1966 | Fox ................................ | 23/230 B |
| 3,632,735 | 1/1972 | Kita et al. .................... | 252/408 X |
| 3,753,925 | 8/1973 | Louderback et al. .......... | 252/408 |
| 3,764,556 | 10/1973 | Kuchmak et al. .............. | 252/408 |
| 3,955,925 | 5/1976 | Proksch et al. ............... | 23/230 B |
| 4,045,176 | 8/1977 | Proksch et al. ............... | 23/230 B |
| 4,127,502 | 11/1978 | Mutti et al. .................. | 23/230 B X |

OTHER PUBLICATIONS

Bernfeld et al., "The Influence of Chem. & Physicochemical Nature of Macromolecular Polyanions on Their Interaction with Human Serum β-Lipoproteins," Journal of Biological Chemistry; Oct. 1960; vol. 235; No. 10; pp. 2852-2859.
Oncley et al.; "A Rapid Method for the Bulk Isolation of β-Lipoproteins from Human Plasma"; Journal of the Amer. Chem. Soc.; vol. 79, No. 13, Jul. 5, 1957; pp. 4666-4671.

*Primary Examiner*—Arnold Turk
*Attorney, Agent, or Firm*—Emhardt & Naughton Woodard, Weikart

[57] ABSTRACT

A lipoprotein diluent useful in the preparation of a standard or reference material for assay procedures which comprises a stabilized aqueous solution of turbidity-potential lipoproteins. The solution contains a preservative including a polyhydroxy cryoprotective agent and/or an antibiotic, and may be used directly as a cholesterol or triglyceride standard or control. The solution may also include other stable components but is free from lipoprotein-degrading enzymes. In accordance with the method of the present invention, a standard or reference material is prepared by adding a diluent containing turbidity-potential lipoproteins to a lyophilized serum base, which contains enzymes.

20 Claims, No Drawings

LIPOPROTEIN DILUENT OR SOLUTION AND METHOD USEFUL IN THE PREPARATION OF ASSAY REFERENCE MATERIALS

BACKGROUND OF THE INVENTION

1. Field of the Invention

The present invention relates to the field of standard or reference materials useful in assay procedures, and more particularly relates to materials and methods for the preparation of such standards which do not display significant turbidity.

2. Description of the Prior Art

The use of serum standards or references in blood chemistry analysis is well known. It is frequently advantageous as a diagnostic aid to determine the level of certain constituents of a patient's blood. This determination is made with the aid of serum standards. The serum standards are commonly stored as a dry powder after lyophilization to be reconstituted at the time of use. Alternatively, they may be frozen and thawed. It is desirable that the lyophilized serum, when reconstituted with an aqueous media, or the frozen serum when thawed, be stable and have substantial optical clarity to minimize interference with the analytical measurement of serum constituents.

Two important blood constituents are triglyceride and cholesterol. It is therefore desirable to prepare a serum standard or a reference material containing triglyceride and/or cholesterol and having good optical clarity for use with analytical testing procedures. The serum should also be stable and easily reconstituted after storage.

The difficulties in photometric analysis which result from turbidity in serum and plasma samples are generally set forth in U.S. Pat. No. 3,853,465, issued to Ruch et al. on Dec. 10, 1974, which is hereby incorporated by reference. In this regard, in our U.S. Pat. No. 3,955,925, issued on May 11, 1976, we disclosed a method for preparing a serum standard which remains stable and optically clear upon lyophilization and reconstitution with aqueous media. In accordance with the method disclosed therein, the pre-beta lipoproteins, beta lipoproteins and chylomicrons are (turbidity potential lipoproteins) removed from human serum by specific precipitation with a metal cation and a polysulfate. Further, in our U.S. Pat. No. 4,045,176, issued on Aug. 30, 1977, we disclosed a method for the preparation of a serum standard having normal or elevated levels of cholesterol and/or triglyceride and being stable and optically clear upon lyophilization and reconstitution. In accordance with the method of the latter patent, isolated non-primate lipoproteins or isolated high density human lipoproteins are added to serum, the serum in certain embodiments having the pre-beta lipoproteins, beta lipoproteins and chylomicrons removed therefrom.

In U.S. Pat. No. 3,274,062, issued to Lou on Sept. 20, 1966, there is disclosed a method for concentrating cholesterol-rich protein constituents of human blood serums. In accordance with the Lou method, the beta lipoproteins are precipitated from human plasma or serum by the addition of "Mepesulfate" and calcium ions. The precipitate is then purified by dialysis and subsequently added to liquid serum to form a high cholesterol standard. The Lou method does not involve the use of a lipoprotein solution to which preservatives have been added as a diluent, and moreover does not disclose the addition of this lipoprotein diluent to a lyophilized serum base. In fact, the supernatant serum from which the beta lipoproteins are removed according to the Lou method is discarded as waste material.

A method for isolating triglyceride-rich concentrate and cholesterol-rich precipitate from egg yolks and human plasma, respectively, is disclosed in U.S. Pat. No. 3,764,556, issued to Kuchmak et al. on Oct. 9, 1973. In accordance with the Kuchmak et al. disclosure, a cholesterol-rich lipid precipitate isolated from human plasma and containing about 75% of the total cholesterol and about 60% of the triglyceride was added to bovine, horse and human serums to provide a control standard having the desired level of lipids. As reported therein, the serum preparations were frozen and thawed three times with the solutions retaining their original transparent appearance. The Kuchmak et al. patent indicates that the lipid fractions must be immediately dissolved in serum at room temperature. The Kuchmak et al. reference does not disclose the inclusion of a preservative with a lipoprotein diluent, nor the adding of a lipoprotein diluent to a lyophilized serum base to provide a serum standard which is free of turbidity and has the desired levels of lipoproteins. Further, there is no teaching in the Kuchmak et al. reference that the lipoprotein fraction be used as a diluent for lyophilized, serum to provide a resulting serum standard which does not display turbidity.

SUMMARY OF THE INVENTION

One aspect of the present invention relates to a lipoprotein solution useful as a standard or reference material and which comprises an aqueous solution of lipoproteins of a type and in an amount which would cause significant turbidity upon lyophilization and reconstitution of the solution. The lipoprotein solution is free from enzymes which would degrade the lipoproteins, and additionally includes a preservative, such as a polyhydroxy cryoprotective agent and/or an antibiotic, typically an antimicrobial agent. Another aspect of the present invention relates to a method for preparing a serum standard or reference material by the addition of a lipoprotein diluent comprising turbidity-potential lipoproteins to a lyophilized serum base. The serum base may contain protein, enzymes, and metabolites. The reconstitution of the serum base with the lypoprotein diluent does not result in a significant increase in the turbidity of the serum standard over reconstitution with water.

It is an object of the present invention to provide a lipoprotein diluent which will remain stable and optically clear for extended periods of time.

Another object of the present invention is to provide a lipoprotein diluent which is useful as a standard or reference material, and moreover which is useful in the preparation of substantially human serum standards or reference materials which do not display significant turbidity.

It is a further object of the present invention to provide a method for the preparation of serum standards or reference materials which results in a serum standard which does not display significant turbidity.

It is another object of the present invention to provide a method for the preparation of serum standards or reference materials which utilizes materials, specifically a lyophilized serum base and a lipoprotein diluent, each of which may be retained for extended periods of time without adversely affecting the optical clarity of the resulting serum standard.

A further object of the present invention is to provide a method for the preparation of serum standards or reference materials, which method is easily and accurately performed to provide serum standards of varying concentrations of the serum constituents, particularly the cholesterol and triglyceride.

Another object of the present invention is to provide a method for the preparation of serum standards or reference materials which utilizes a lipoprotein diluent which contains those serum constituents desired to be measured in the produced serum and which constituents would produce turbidity in the prepared serum upon freezing and thawing or upon lyophilization and reconstitution, the diluent being maintainable in the liquid state for prolonged periods without adversely affecting the optical clarity of the prepared serum.

Further objects and advantages of the present invention will become apparent from the Description of the Preferred Embodiments which follows.

DESCRIPTION OF THE PREFERRED EMBODIMENTS

As previously noted, it has been found desirable for various reasons to provide a serum standard or reference material having normal or elevated levels of triglyceride or cholesterol and which does not display significant turbidity. Concurrently, it is desirable that the serum standard or reference material be conveniently stored prior to use, and the typical methods used for storage purposes include freezing or lyophilization. However, it has been found that serum standards having the normal levels of beta lipoproteins, pre-beta lipoproteins and chylomicrons display significant turbidity upon lyophilization and reconstitution. A variety of approaches have been suggested in the prior art for overcoming this problem. We have disclosed, in the previously-mentioned patents, procedures for overcoming this problem which include the use of isolated, high density human lipoproteins or isolated non-primate lipoproteins in lieu of or in addition to the normally present lipoproteins. Others have proposed the addition of surfactants to enhance the solubility of the lipoproteins present in the serum standard. An alternate approach has been to substitute artificial or otherwise equivalent compounds for the lipoproteins. In accordance with the present invention, a lipoprotein diluent and related method are disclosed with provide a serum standard which is conveniently stored prior to use and which is stable and optically clear upon preparation.

In accordance with the present invention, a lipoprotein diluent is provided which comprises an aqueous solution of turbidity-potential lipoproteins in an amount sufficient to cause turbidity upon lyophilization of the solution. For the purposes herein, the term "turbidity-potential lipoproteins" is intended to mean those lipoproteins which are associated with the turbidity produced in serum which is frozen and thawed or which is lyophilized and reconstituted with an aqueous media. The association of beta lipoproteins, pre-beta lipoproteins and chylomicrons with serum turbidity is described in our U.S. Pat. No. 4,045,176, issued on Aug. 30, 1977, which we hereby specifically incorporate by reference.

The lipoprotein diluent of the present invention includes a significant amount of the turbidity-potential lipoproteins, the term significant amount being used herein to mean an amount sufficient to cause turbidity upon lyophilization and reconstitution of the serum. As will be more fully described below, a potential turbidity problem is avoided since the turbidity-potential lipoproteins are not subjected to lyophilization. It will be readily appreciated that the necessity of the diluent would be eliminated if the amount of turbidity-potential lipoproteins in the serum standard was insufficient to cause turbidity upon freezing or lyophilization of the standard, since the minimal amount of lipoproteins in that case would permit the entire serum standard, including the lipoproteins, to be frozen or lyophilized without producing large amounts of turbidity in the serum standard. This, for example, was the case in U.S. Pat. No. 3,764,556, issued to Kuchmak et al. on Oct. 9, 1973 and previously cited. As stated in that patent, a lipoprotein fraction was added to bovine serum and the resultant preparation, upon freezing and thawing three times, retained its original transparency. As is well recognized, the use of turbid serum standards or reference materials can result in inaccurate readings in typical assay procedures, which is readily understandable in view of the use of photometric analysis in obtaining such readings. Depending upon the particular application, especially the constituent being assayed and the procedure being utilized, the degree of turbidity in the standard or reference material which may be tolerated will vary. The amount of turbidity which would be acceptable in a particular application is readily determined in view of the degree of accuracy required from the particular assay procedure, more particularly the percentage of accuracy desired in evaluating the level or amount of the measured constituent, and consequently the amount of error which can be permitted due to the turbidity of the serum standard.

The lipoprotein diluent of the present invention is further characterized by being free from lipoprotein-degrading enzymes. It is necessary that the lipoprotein diluent be free from enzymes which would break down the lipoproteins prior to use of the diluent. These enzymes, such as lipoprotein lipase and lipase, are well known in the art.

The lipoprotein diluent of the present invention is still further characterized in that it may be used directly as a cholesterol or triglyceride standard or control under certain conditions. For example, see the specific examples set forth hereinbelow.

Included with the lipoprotein diluent is a preservative to ensure the stability and integrity of the lipoprotein solution. The preservative may comprise a polyhydroxy cryoprotective agent, an antibiotic or antiseptic agent or both. The polyhydroxy cryoprotective agent is included if it is possible or likely that the diluent will be subjected to low temperatures and might freeze. It is important, as previously noted, that the diluent be prevented from freezing without the polyhydroxy cryoprotective agent since the turbidity-potential lipoproteins present in the diluent would cause the thawed diluent, and any serum standard produced therewith, to be turbid and to measure inaccurately in assay procedures. The polyhydroxy cryoprotective agent could be any of a variety of chemicals, although those specifically known to be useful in biological preparations are preferred. Examples of polyhydroxy cryoprotective agents which could be combined in the lipoprotein diluent are ethylene glycol, diethylene glycol, propylene glycol and butylene glycol, sorbitol, glucose, lactose and sucrose.

The preservative may alternatively or additionally include an antibiotic such as an antibacterial agent which may be bactericidal and/or bacteriostatic. Examples of antibacterial agents which are useful as a preservative for the lipoprotein diluent are penicillin, gentimycin, tetracycline and bacitracin. An antifungal agent, which may be either fungicidal, fungistatic or both, may also be added if necessary or desired.

In addition to the turbidity-potential lipoproteins and the preservatives, the lipoprotein diluent may contain a variety of additional constituents. Such additional constituents primarily should be stable in the aqueous solution, and should not operate to degrade or otherwise interfere with the lipoproteins and the preservatives in the solution. Typically, the additional constituents of the lipoprotein diluent would be items which would be normal or potential blood serum constituents, and which would therefore desirably be measured in the blood serum assay procedures. Addition of these constituents to the diluent would permit the concentrations of these constituents in a serum prepared with the diluent to be accurately and consistently established. In particular, a carbonate compound would desirably and preferably be included in the lipoprotein diluent. The presence of the carbonate ions is desirable since carbonates are typically one serum constituent which would be measured in assay procedures. Moreover, the carbonate operates in the lipoprotein diluent as a buffering agent. Examples of carbonate compounds which could be utilized for this purpose are sodium bicarbonate, tris bicarbonate, and ammonium bicarbonate. The carbonate also provides a dilute salt solution needed to prevent the lower density lipoproteins from precipitating. The molarity of the salt solution is variable, with a 0.03 M solution being preferred. Numerous other salts are similarly useful, including: sodium chloride, ammonium chloride, tris chloride, tris acetate, sodium acetate, and ammonium acetate, and tris-ethylenediamine tetraacetic acid.

The lipoprotein diluent of the present invention may be obtained in a variety of fashions. The diluent contains turbidity-potential lipoproteins, and may additionally include the alpha lipoproteins which are not associated with turbidity in serum which has been frozen and thawed or which has been lyophilized and reconstituted. The lipoprotein diluent is preferably prepared by obtaining a lipoprotein fraction from plasma or serum, whether human or otherwise, or from egg yolks. Depending upon the procedure employed, as shown by the examples herein, a lipoprotein fraction may be obtained which contains primarily one type of lipoprotein or contains a mixture of some or all of the lipoprotein types. The lipoprotein fraction is combined with selected amounts of water, carbonate or other dilute salt solutions, and/or preservatives as previously described. The relative amounts or ratio of the various types of lipoproteins, and therefore of the triglyceride and cholesterol in the diluent, as well as the relative amount of water, carbonates, polyhydroxy cryoprotective agents, preservatives and other constituents, may be readily controlled to provide a lipoprotein diluent having desired constituent levels.

In another aspect, the present invention provides a method for the preparation of a standard or reference material for use in assay procedures, which material does not display turbidity and therefore does not interfere or otherwise give inaccurate readings in typical assay procedures. In accordance with this method, a lipoprotein diluent generally of the above-described type is added to a lyophilized serum base. It is preferable that the lipoprotein diluent contain a preservative.

The serum base contains enzymes, and particularly those enzymes which would degrade the lipoproteins contained in the diluent. It is frequently desirable to have a serum standard which contains certain enzymes since these constituents may be the subject of assay measurements. A primary feature of the method of the present invention is that it provides a serum standard or reference material which includes lipoproteins and lipoprotein-degrading enzymes, but which is not turbid due to lyophilization and reconstitution of a lipoprotein-containing serum and which does not permit the degradation of the lipoproteins by the enzymes prior to the preparation of the serum standard. It will be appreciated that if the lipoprotein-degrading enzymes are not desired or rquired to be in the final serum standard, it would be possible to provide a serum standard simply by removing or destroying these enzymes. However, in accordance with the present invention, the time and expense associated with the removal or destruction of the enzymes, assuming that such may be fully accomplished, are obviated. Moreover, the method of the present invention provides for the separation of the lipoproteins from the lipoprotein-degrading enzymes and permits a portion of the ingredients for the final serum standard to be lyophilized to increase constituent stability, and facilitate storage, handling and transportation.

In addition to the enzymes, the serum base may comprise a variety of materials, and particularly might include other normal serum constituents. As previously discussed, beta lipoproteins, pre-beta lipoproteins and chylomicrons are associated with turbidity in serum which has been frozen and thawed or lyophilized and reconstituted. The serum base utilized by the method of the present invention is lyophilized for storage and preservation purposes. Thus, the presence of the turbidity-potential lipoproteins, i.e. beta lipoproteins, pre-beta lipoproteins and chylomicrons, unless limited in amount, would result in a prepared serum standard or reference material which would display turbidity. The preferred method of the present invention therefore utilizes a lyophilized serum base which is free from the turbidity-potential lipoproteins in significant amounts, or in other words free from an amount sufficient upon reconstitution of the lyophilized serum base with the diluent to cause analytical error when the resultant serum is used as a standard.

The serum base may be obtained from a variety of sources. A particularly convenient source of the serum base is the serum from which a lipoprotein fraction of the lower density lipoproteins has been removed. Thus, the two materials utilized in the method of the present invention may be conveniently obtained by removing some (the lower density) or all of the lipoproteins from a serum sample, the lipoprotein fraction being utilized to prepare the diluent and the remaining serum being utilized to provide the serum base. Alternatively, it has been found that due to the relative proportions of the high and low density lipoproteins in certain non-primate blood serums, such as bovine serum, the non-primate serum may be directly lyophilized and reconstituted without turbidity resulting. Thus, these non-primate serums, preferably bovine serum, may be directly lyophilized to form the serum base utilized in the method of the present invention. This is particularly advantageous when elevated levels of cholesterol or triglyceride are desired in the final serum standard since the serum base will already have a substantial amount of lipoproteins in addition to those added by the combination with the serum base of the lipoprotein diluent.

A number of additional materials may be included in the lipoprotein diluent or in the serum base without adversely affecting the serum standard produced by the method of the present invention. In one aspect, the inclusion of such additional constituents is preferablse in the sense that the constituents would already be present and the unnecessary removal thereof is avoided. In general, these additional constituents may be contained in either or both of the diluent and the serum base, although the method of preparing these two materials might logically dictate the location where the additional constituents would be found. Thus, if the serum base is prepared by the removal of lipoproteins from human serum, the serum base would typically include most or all of the other normally-present serum components. It is preferablse that the lipoprotein diluent and the serum base, either individually or together, include additional normal serum constituents in amounts sufficient to be measurable in common assay procedures, and these additional constituents may include the following: calcium, sodium, chloride, potassium, urea, uric acid, inorganic phosphorus, glucose, BUN, LDH, bilirubin and albumin. These components may be added to desired levels to either the diluent or the serum base, or may appear in one or the other due to the method of preparation. As will be readily appreciated, the concentration of these constituents as well as those previously enumerated, such as the cholesterol, triglyceride and enzymes, may be readily controlled by appropriate preparation of the lipoprotein diluent and the serum base and by appropriate combination of the two for the serum standard.

EXAMPLE 1

A bovine lipoprotein extract was obtained in the following manner. To bovine serum, calcium chloride was added to achieve a 0.05 molar calcium cation concentration. The pH was adjusted to 7.2 and dextran sulfate was added to achieve a 0.5 g/l concentration. The solution was allowed to stand at 5° C. for 2 hours. The resulting first precipitate fraction comprising mainly low-density lipoproteins (beta-lipoprotein) was removed by centrifugation and the remaining first supernatant was saved.

The first precipitate fraction was redissolved by adding the low-density lipoprotein-dextran sulfate complex to an equal volume of 1.5 M NaCl. The resulting solution was then diluted to one thirtieth the original serum volume by the addition of 0.75 M NaCl. The preparation was stirred for one hour and insoluble matter was removed by centrifugation. The supernatant was then diluted seven-fold with a 0.05 M $CaCl_2$ and 0.3 g/l dextran sulfate solution. The resulting, second precipitated complex was then isolated by centrifugation and the supernatant was discarded.

The second precipitated lipoprotein-dextran sulfate complex was redissolved by adding an equal volume of 30 g/dl $BaCl_2$ and stirring for one hour at 5° C. The dextran sulfate was thereby precipitated and was removed by centrifugation. The clear supernatant containing the lipoproteins was then dialyzed against 6 g/l NaCl and then against 0.03 N $NaHCO_3$, and any resulting precipitates were removed by centrifugation. A clear yellow solution representing a concentrated solution of cholesterol and a lesser concentration of triglycerides was produced. The solution was miscible in all proportions with a variety of salt solutions including 0.03 N $NaHCO_3$, 0.03 M $NH_{4s}HCO_3$, 0.03 M sodium acetate and 0.03 M lithium acetate. The solution was found to be stable for at least two weeks at 37° C. and for several months at 5° C. and was shown useful for standards and references for cholesterol and triglyceride assays.

EXAMPLE 2

The procedure of Example 1 was followed with the first supernatant. To the first supernatant was added calcium chloride to obtain a concentration of calcium cation of 0.25 M. The pH was adjusted to 7.2 and additional dextran sulfate was added to achieve a concentration of 2.5 g/l. The solution was allowed to stand for two hours and the resulting third precipitate fraction, consisting of essentially a complex of dextran sulfate and high-density lipoprotein (alpha-lipoprotein) and a minor amount of low-density lipoprotein (beta-lipoprotein), was removed by centrifugation.

The third precipitate fraction of bovine lipoprotein and dextran sulfate was dissolved in an equal volume of a 1.5 M NaCl solution. The resulting solution was then diluted to one-thirtieth (1/30) the original serum volume by the addition of 0.75 M NaCl. The turbid solution was diluted seven-fold with 0.10 M $CaCl_2$ and 0.3 g/l dextran sulfate to again precipitate the lipoprotein-dextran sulfate complex which was collected by centrifugation.

An equal volume of 30 g/dl $BaCl_2$ was added to the precipitate and the mixture was stirred for two hours. The dextran sulfate thereby precipitated was removed by centrifugation and the clear supernatant was dialyzed successively against distilled water and 0.03 N $NaHCO_3$. Any additional precipitate that formed was removed by centrifugation.

The resulting clear golden solution was a concentrate of cholesterol with lesser amounts of triglyceride. The solution was stable for several months at 5° C., and was miscible with water and with 0.03 N $NaHCO_3$ in all proportions. The solution, so prepared, was shown particularly useful for standards and references for cholesterol assays.

EXAMPLE 3

A bovine lipoprotein extract was obtained according to the technique of Jonas as described in the Journal of Biological Chemistry, Volume 247, pages 7767 et seq. Briefly, bovine serum was allowed to clot at room temperature and was centrifuged at 60,000 rpm for about 24 hours. A first lipoprotein fraction of primarily low-density lipoproteins and chylomicrons was then removed from the top of the solution and saved. A further top portion was removed and discarded and contained a mixture of low and high density material. The remaining solution was centrifuged under the same conditions and a second lipoprotein fraction comprising primarily high density lipoproteins was drawn off the top.

EXAMPLE 4

A bovine lipoprotein extract was obtained according to the procedure of Oncley et al. as disclosed in the Journal of the American Chemical Society, Volume 79, pages 4666 et seq. Briefly, a 0.5% (w/v) solution of dextran sulfate solution was added with stirring to bovine serum. A lipoprotein-dextran sulfate precipitate was allowed to form and was separated by centrifugation. The precipitate was then suspended in a 2.0 M sodium chloride solution and was ultracentrifuged. The liquid separated into four distinct layers.

Portions of the top three layers were individually and collectively dialyzed against 1% $BaCl_2$ and water. The top layer contained the lowest density lipoproteins and successively lower layers contained progressively higher density fractions of lipoproteins.

EXAMPLES 5-16

The procedures of Examples 1-4 were followed exactly except the lipoprotein fractions were obtained from human, hog, horse, chicken and dog serums.

EXAMPLES 17-64

The lipoprotein fractions prepared in accordance with Examples 1-16 were diluted in varying proportions to obtain solutions of differing concentrations of cholesterol and triglyceride. To samples of each of the diluted solutions were added amounts of 0.03 N $NaHCO_3$, 0.03 N tris bicarbonate and/or 0.03 M $NH_4HCO_3$ sufficient to provide measureable amounts of carbonate ions in normal assay procedures.

Portions of each of these prepared solutions were combined with antibacterial agents, penicillin and gentamicin, at typical levels. The resulting preparations were stable and remained essentially bacteria-free for extended periods. Other portions of the diluted solutions were combined with ethylene glycol to a final concentration of 1% ethylene glycol and still other portions were combined with ethylene glycol (1% final concentration), penicillin and gentamicin. The resulting preparations may be frozen for extended periods. Upon thawing, the solutions are optically clear.

EXAMPLE 65

The yolk of an egg was separated from the egg white and yolk sac, and was diluted five fold with 0.03 N NaCl and the pH was adjusted to 5.5 with acetic acid. The mixture was allowed to stand at 5° C. for 2 hours and was centrifuged. The clear supernatant was decanted and dialyzed against 0.03 M $NaHCO_3$. Any additional precipitate was removed by centrifugation. The resulting clear yellow solution was stable for two weeks at 37° C., and for several months at 5° C. This preparation contained a concentrated amount of triglyceride and much smaller amounts of cholesterol. The preparation was miscible in all proportions in dilute salt solutions such as 0.03 N $NaHCO_3$, 0.03 NaCl, 0.03 tris bicarbonate, and 0.03 ammonium bicarbonate. The preparation was shown particularly useful for standards and references for triglyceride.

A portion of the prepared solution was combined with antibacterial agents, penicillin and gentamicin, at typical levels. The resulting preparation was stable and remained essentially bacteria-free for extended periods. Another portion of the diluted solution was combined with ethylene glycol to a final concentration of 1% ethylene glycol and still another portion was combined with ethylene glycol (1% final concentration), penicillin and gentamicin. The resulting preparations may be frozen for extended periods. Upon thawing, the solutions are optically clear.

EXAMPLES 66-81

The procedure of Examples 17-64 was followed exactly except that different antibiotics and polyhydroxy cryoprotective agents were used. The antibiotics used included antibacterial agents such as tetracyclines, bacitracin, and other antibiotics such as fungizone, sodium azide; and the polyhydroxy cryoprotective agents included diethylene glycol, propylene glycol, butylene glycol, glucose, lactose, sucrose, and sorbitol. Similar results were obtained.

EXAMPLES 82-161

A normal 1000 ml. pooled human blood plasma sample was obtained. The plasma was then prepared as described in our U.S. Pat. No. 3,955,925. Calcium chloride was added to the plasma to achieve a 0.04 molar concentration of calcium cation in the plasma. The pH was adjusted to 7.4 using 1.5 ml to 6 N NaOH. The mixture was then heated to 37° C. and 1 ml. of topical bovine thrombin (1000 NIH units per ml) was added. The plasma was allowed to clot and the serum was then expressed from the clot. Dextran sulfate was added to the serum to achieve a concentration of 0.2 g/l. A flocculent lipoprotein-complex precipitate was formed at pH 7.4. The precipitate was subsequently removed and discarded, and the resulting supernatant serum was optically clear. The excess calcium was removed by dialysis, treatment with oxalate or ion exchange techniques.

The serum, which contained the normal enzymes but which was free from a significant amount of turbidity-potential lipoproteins, was lyophilized to a powdered form and stored at 5° C. for several weeks. After storage, separate portions of the powdered serum were reconstituted with solutions of each of the lipoprotein fractions prepared in accordance with Examples 1-81, the lipoprotein fractions being enzyme free as a result of the preparation procedures. The reconstituted serum was optically clear and measured well in normal assay procedures.

EXAMPLE 162—Use of Human Serum

The procedure of Examples 82-161 was repeated except untreated human serum was lyophilized for storage, at 5° C. for several weeks. After storage, lipoprotein fractions, prepared in accordance with Examples 1-81, were added to the lyophilized serum. The resultant serum had elevated levels of cholesterol and/or triglyceride and possessed good optical clarity and measured well in normal assay procedures.

EXAMPLES 163 and 164

Portions of the lipoprotein extracts prepared in the manners described in EXAMPLES 1-81 were diluted 1 to 5 with distilled water or weak salt solutions such as 0.03 N $NaHCO_3$ under sterile conditions. The diluted extracts were added as diluents to reconstitute lyophilized bovine, horse, and dog serums. The resulting serums were clear, with the bovine serum preparation showing particularly excellent clarity.

While there have been described above the principles of this invention in connection with specific examples, it is to be clearly understood that this description is made only by way of example and not as a limitation in the scope of the invention.

We claim:

1. A method for the preparation of a standard or reference material for use in assay procedures which comprises adding a lipoprotein diluent containing a significant amount of turbidity-potential lipoprotein and being essentially free from lipoprotein-degrading enzymes to a lyophilized serum base which is free from a significant amount of turbidity-potential lipoproteins.

2. The method of claim 1 in which the diluent is enzyme free.

3. The method of claim 1 in which the diluent further comprises a salt.

4. The method of claim 1 in which at least one of the lipoprotein diluent and the serum base includes additional normal serum constituents in an amount sufficient to be measureable in common assay procedures.

5. The method of claim 1 in which the lipoprotein diluent includes carbonate ions in an amount sufficient to be measureable in normal assay procedures.

6. The method of claim 5 in which the diluent includes a carbonate compound selected from the group consisting of sodium bicarbonate, tris bicarbonate and ammonium bicarbonate.

7. The method of claim 1 in which the serum base comprises human blood serum from which the turbidity-potential lipoproteins have been substantially removed.

8. The method of claim 7 in which the lipoprotein diluent comprises a lipoprotein fraction removed from blood serum.

9. The method of claim 1 in which the serum base comprises non-primate animal serum.

10. The method of claim 9 in which the serum base comprises bovine serum.

11. The method of claim 1 in which the lipoprotein diluent comprises a blood serum lipoprotein fraction.

12. The method of claim 11 in which the diluent comprises a non-primate animal serum lipoprotein fraction.

13. The method of claim 12 in which the lipoprotein diluent comprises a hog serum lipoprotein fraction.

14. The method of claim 12 in which the lipoprotein diluent comprises a bovine serum lipoprotein fraction.

15. The method of claim 1 in which the lipoprotein diluent includes a preservative.

16. The method of claim 15 in which the preservative comprises an antibiotic.

17. The method of claim 16 in which the antibiotic comprises an antibacterial agent.

18. The method of claim 15 in which the preservative comprise a polyhydroxy cryoprotective agent.

19. The method of claim 18 in which the polyhydroxy cryoprotective agent is selected from the group consisting of ethylene glycol, diethylene glycol, propylene glycol, butylene glycol, sorbitol, glucose, lactose and sucrose.

20. The method of claim 19 in which the polyhydroxy cryoprotective agent is selected from the group consisting of sorbitol, glucose, lactose and sucrose.

* * * * *